United States Patent
Beeson

(10) Patent No.: US 9,918,018 B2
(45) Date of Patent: Mar. 13, 2018

(54) DYNAMIC RANGE ENHANCEMENT SYSTEMS AND METHODS FOR USE IN WELDING APPLICATIONS

(71) Applicant: Illinois Tool Works Inc., Glenview, IL (US)

(72) Inventor: Richard Beeson, Glenview, IL (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 15/412,942

(22) Filed: Jan. 23, 2017

(65) Prior Publication Data
US 2017/0289424 A1    Oct. 5, 2017

Related U.S. Application Data

(60) Provisional application No. 62/317,891, filed on Apr. 4, 2016.

(51) Int. Cl.
  *H04N 5/235* (2006.01)
  *A61F 9/06* (2006.01)
  (Continued)

(52) U.S. Cl.
  CPC ............ *H04N 5/2355* (2013.01); *A61F 9/06* (2013.01); *B23K 9/0953* (2013.01);
  (Continued)

(58) Field of Classification Search
  CPC ............ H04N 5/2355; H04N 5/23293; H04N 5/2258; H04N 5/332; H04N 5/35545;
  (Continued)

(56) References Cited

U.S. PATENT DOCUMENTS 6,204,881 B1   3/2001   Ikeda
6,242,711 B1 *  6/2001   Cooper ............... A61F 9/06
                                                 219/130.01
(Continued)

FOREIGN PATENT DOCUMENTS

JP    2001 138049 A    5/2001
JP    2009 160624 A    7/2009
WO    2016/044874 A1   3/2016

OTHER PUBLICATIONS

European Patent Office, Communication with extended European search reoprt in Application No. 17160032.3-1902, dated Sep. 15, 2017 (26 pages).

(Continued)

*Primary Examiner* — Pritham Prabhakher
(74) *Attorney, Agent, or Firm* — McAndrews, Held & Malloy, Ltd.

(57) ABSTRACT

Dynamic range enhancement methods and systems for display for use welding applications are described. A display system in a dynamic range enhancement system can include, for example, a splitter, a high density filter, a low density filter, a first image sensor, a second image sensor, a graphical circuit, and a display. The high density filter and the first image sensor can be disposed in a first path. The low density filter and the second image sensor can be disposed in a second path. The first image sensor can receive filtered electromagnetic waves from the high density filter. The second image sensor can receive filtered electromagnetic waves from the low density filter. The graphic circuit can combine the signals from the first image sensor and the second image sensor to provide a high dynamic range image or video that is displayed on the display of a welding helmet, for example.

29 Claims, 7 Drawing Sheets

(51) Int. Cl.
     B23K 9/095    (2006.01)
     G02B 5/20     (2006.01)
     G02B 27/01    (2006.01)
     G02F 1/133    (2006.01)
     G06F 3/01     (2006.01)
     H04N 5/225    (2006.01)
     H04N 5/232    (2006.01)
     H04N 5/355    (2011.01)
     B23K 25/00    (2006.01)
     H04N 5/33     (2006.01)
     G06T 5/50     (2006.01)

(52) U.S. Cl.
     CPC ............ *B23K 9/0956* (2013.01); *B23K 25/00*
           (2013.01); *G02B 5/20* (2013.01); *G02B*
           *27/017* (2013.01); *G02F 1/13318* (2013.01);
           *G06F 3/011* (2013.01); *H04N 5/2258*
           (2013.01); *H04N 5/23293* (2013.01); *H04N*
           *5/332* (2013.01); *H04N 5/35545* (2013.01);
           *G06T 5/50* (2013.01); *H04N 5/23232*
           (2013.01)

(58) Field of Classification Search
     CPC ......... G06F 3/011; G02B 27/017; G02B 5/20;
           G02F 1/13318; B23K 9/0956; B23K
           9/0953; A61F 9/06
     USPC ...................................... 348/218.1, 374–376
     See application file for complete search history.

(56)           References Cited

U.S. PATENT DOCUMENTS 8,009,229 B1 *  8/2011  Peterson ............... A42B 3/042
                                                          345/8
     8,502,866 B2 *  8/2013  Becker .................... A61F 9/06
                                                          345/8
     9,073,138 B2 *  7/2015  Wills ................. B23K 9/0956
     9,566,192 B2 *  2/2017  Becker .................... G06F 3/005
     9,666,160 B2 *  5/2017  Patel ..................... G09G 5/006
     9,685,099 B2 *  6/2017  Boulware ............. G09B 19/24
     9,773,429 B2 *  9/2017  Boulware ............. G09B 19/24
     2009/0094721 A1 * 4/2009  Becker .................... A61F 9/067
                                                          2/8.8
     2009/0231423 A1   9/2009  Becker
     2011/0251838 A1 * 10/2011  Huh ...................... A61F 9/067
                                                          704/8
     2012/0291172 A1 * 11/2012  Wills ................. B23K 9/0956
                                                          2/8.2
     2013/0215281 A1 * 8/2013  Hobby ................... G06F 3/005
                                                          348/207.1
     2013/0291271 A1 * 11/2013  Becker .................. G06F 3/005
                                                          2/8.2
     2014/0134580 A1 * 5/2014  Becker ................... G09B 9/00
                                                          434/234
     2016/0267806 A1 * 9/2016  Hsu ..................... G09B 19/24

OTHER PUBLICATIONS

Cameron Serles: "Why Weld Cameras Need High Dynamic Range Imaging", Apr. 10, 2013, XP055269605, retrieved from the internet: URL:http://blog.xiris.com/blog/bid/258666/Why-Weld-Cameras0Need-High-Dynamic-Range-Imaging [retrieved on Apr. 29, 2016] *the whole document (3 pages).

* cited by examiner

DYNAMIC RANGE ENHANCEMENT SYSTEMS AND METHODS FOR USE IN WELDING APPLICATIONS

RELATED APPLICATIONS

The present application claims priority to and benefit from U.S. Application No. 62/317,891, filed Apr. 4, 2016. The above-identified application is hereby incorporated herein by reference in its entirety.

BACKGROUND

Welding is a process that has increasingly become ubiquitous in all industries. While such processes can be automated in certain contexts, a large number of applications continue to exist for manual welding operations. The success of these welding operations relies heavily on the ability of the operator to clearly see the arc, the weld, and the workpiece using welding headwear that simultaneously protects the eyes of the operator.

This can be difficult since the range of luminosity is great from the arc, which is intensely bright, to the weld and/or the workpiece, which are substantially less bright or are merely ambient bright. The welding headwear can employ a fixed, dark shade lens to reduce the intensity of the arc; however, the weld and the workpiece would be darkened as well, thereby reducing the visible details in those areas. Of course, a fixed, less dark shade lens would allow more light to come in from the less bright areas or the ambient bright areas; however, the operator would be exposed to a greater arc intensity, thereby risking the eye safety of the operator, and the greater arc intensity would effectively bleach out any details in the less bright areas or the ambient bright areas.

BRIEF SUMMARY

Dynamic range enhancement systems and methods for use in welding applications are provided, substantially as illustrated by and/or described in connection with at least one of the figures, as set forth more completely in the claims.

DETAILED DESCRIPTION

As utilized herein the terms "circuits" and "circuitry" refer to physical electronic components (e.g., hardware) and any software and/or firmware ("code") which can configure the hardware, be executed by the hardware, and or otherwise be associated with the hardware. As used herein, for example, a particular processor and memory can include a first "circuit" when executing a first one or more lines of code and can include a second "circuit" when executing a second one or more lines of code. As utilized herein, "and/or" means any one or more of the items in the list joined by "and/or". As an example, "x and/or y" means any element of the three-element set $\{(x), (y), (x, y)\}$. In other words, "x and/or y" means "one or both of x and y". As another example, "x, y, and/or z" means any element of the seven-element set $\{(x), (y), (z), (x, y), (x, z), (y, z), (x, y, z)\}$. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry includes the necessary hardware and code (if any is necessary) to perform the function, regardless of whether performance of the function is disabled or not enabled (e.g., by a user-configurable setting, factory trim, etc.).

Figure 1:
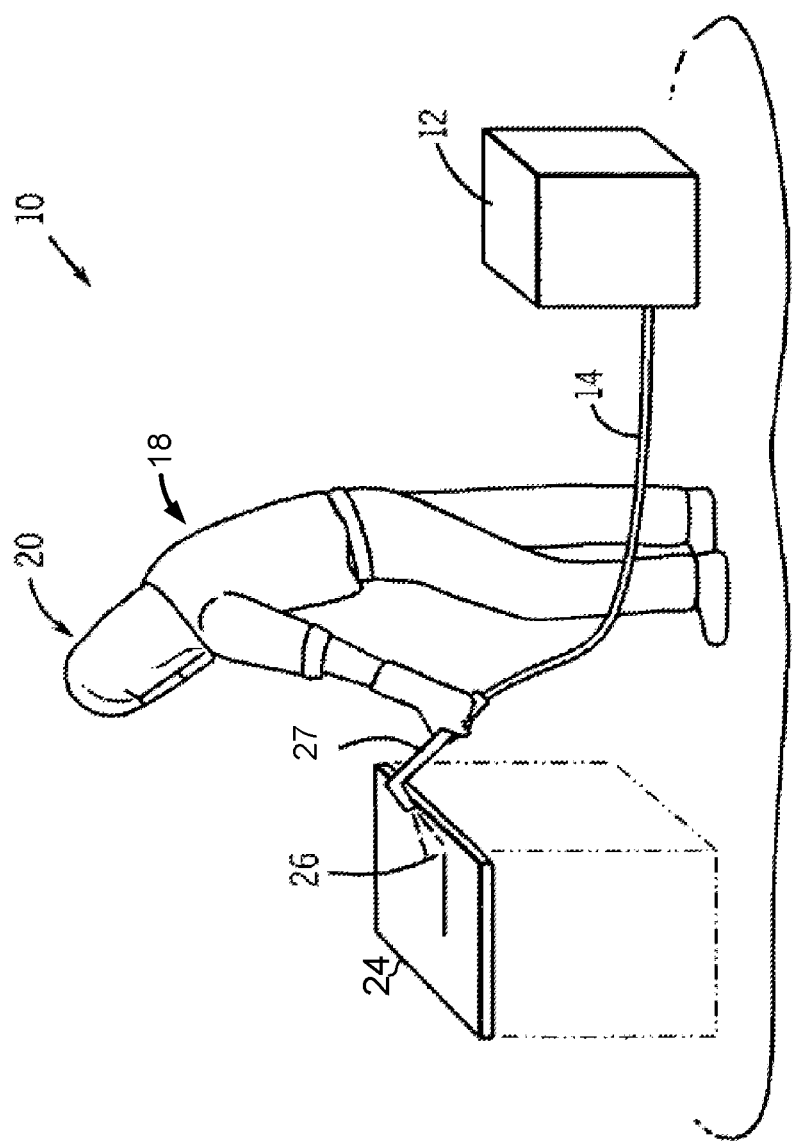
FIG. 1 shows an exemplary arc welding system in accordance with aspects of this disclosure.

Referring to FIG. 1, there is shown an example welding system 10 in which an operator 18 is wearing welding headwear 20 and welding a workpiece 24 using a torch 27 to which power, for example, is delivered by equipment 12 via a conduit 14. The equipment 12 can include, for example, one or more of the following: a welding power source, an inert shield gas source, and a wire feeder for welding applications in which wire and/or filler material is provided automatically. The equipment 12 can provide, for example, one or more of the following to the torch 27: power, voltage, current, shielding gas, wire, and filler material.

The welding system 10 of FIG. 1 can be configured to form a weld joint by any known technique including, for example, flame welding techniques such as oxy-fuel welding and electric welding techniques such as, for example, shielded metal arc welding (e.g., stick welding), metal inert gas welding (MIG), tungsten inert gas welding (TIG), plasma arc welding, and resistance welding.

Optionally in any embodiment, the welding equipment 12 can be arc welding equipment that provides a direct current (DC) or alternating current (AC) to a consumable or non-consumable electrode of the torch 27. The electrode delivers the current to the point of welding on the workpiece 24. In the welding system 10, the operator 18 controls the location and operation of the electrode by manipulating the torch 27 and triggering the starting and stopping of the current flow. When current is flowing, an arc 26 is developed between the electrode and the workpiece 24. The conduit 14 and the electrode thus deliver current and/or voltage sufficient to create the arc 26 between the electrode and the workpiece 24. The arc 26 locally melts the workpiece 24 and/or welding wire or rod (e.g., the electrode in the case of a consumable electrode or a separate wire or rod in the case of a non-consumable electrode) supplied to the weld joint at the point of welding between electrode and the workpiece 24, thereby forming a weld joint when the metal cools.

Figure 2:
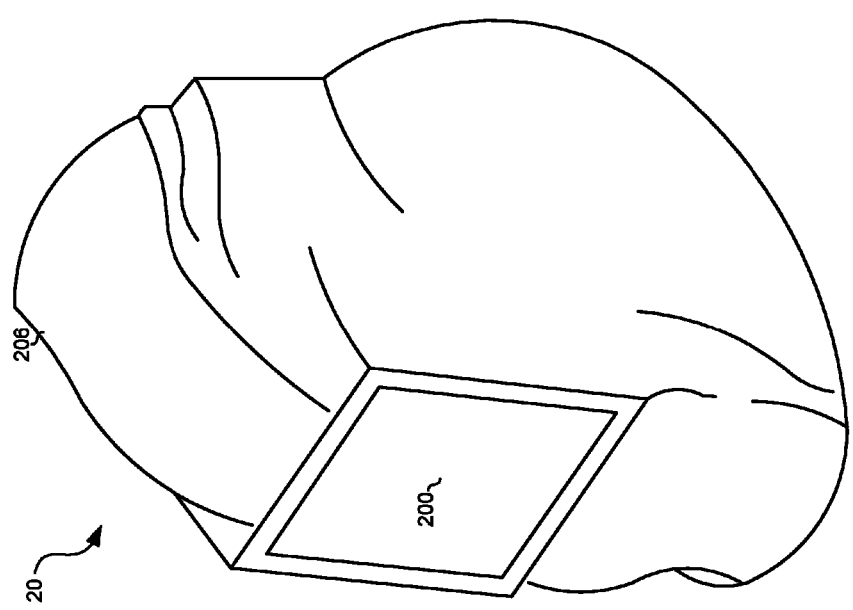
FIG. 2 shows example welding headwear in accordance with aspects of this disclosure.
Figure 3A:
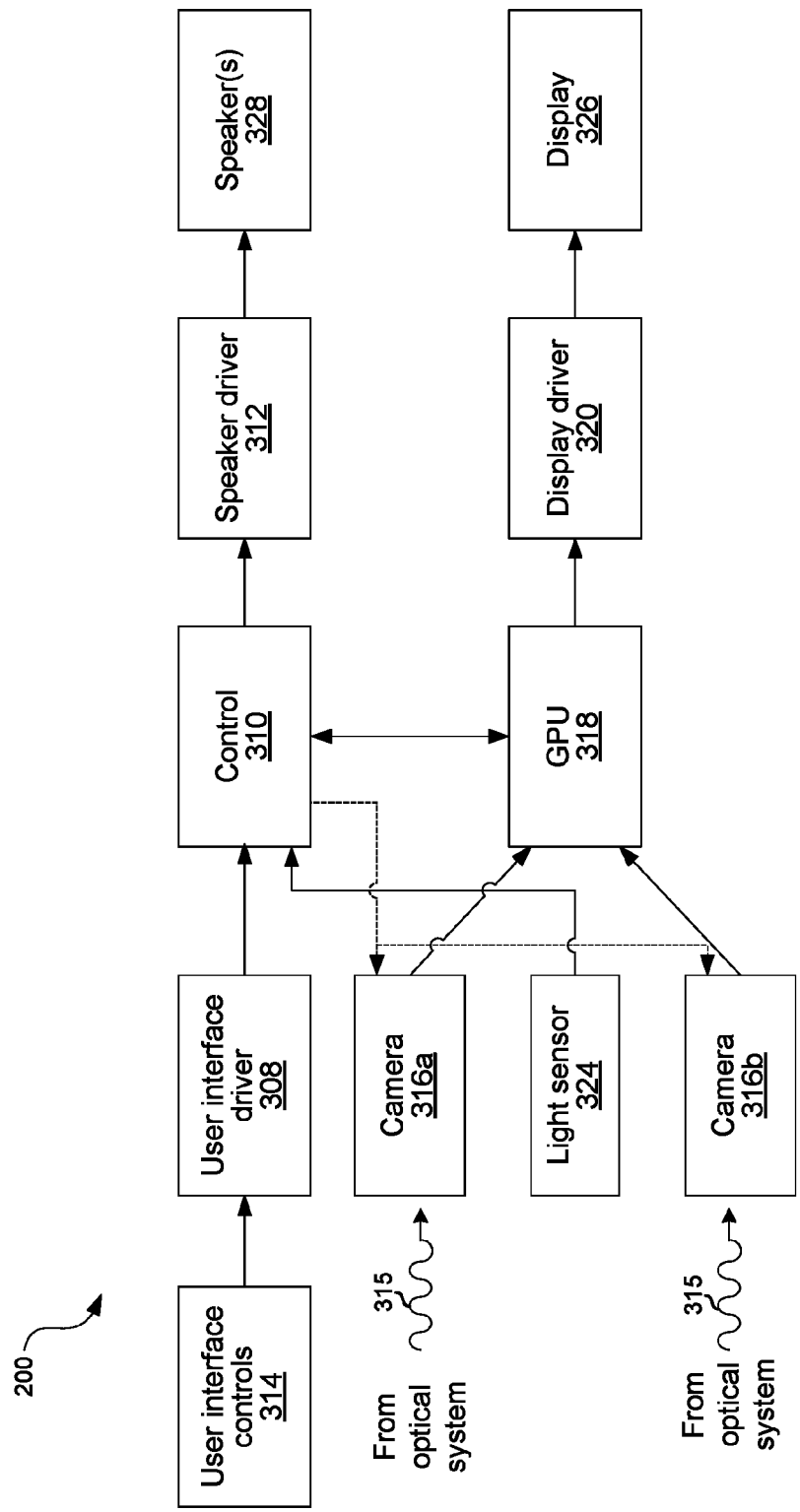
FIG. 3A shows example circuitry of the welding headwear of FIG. 2.
Figure 3B:
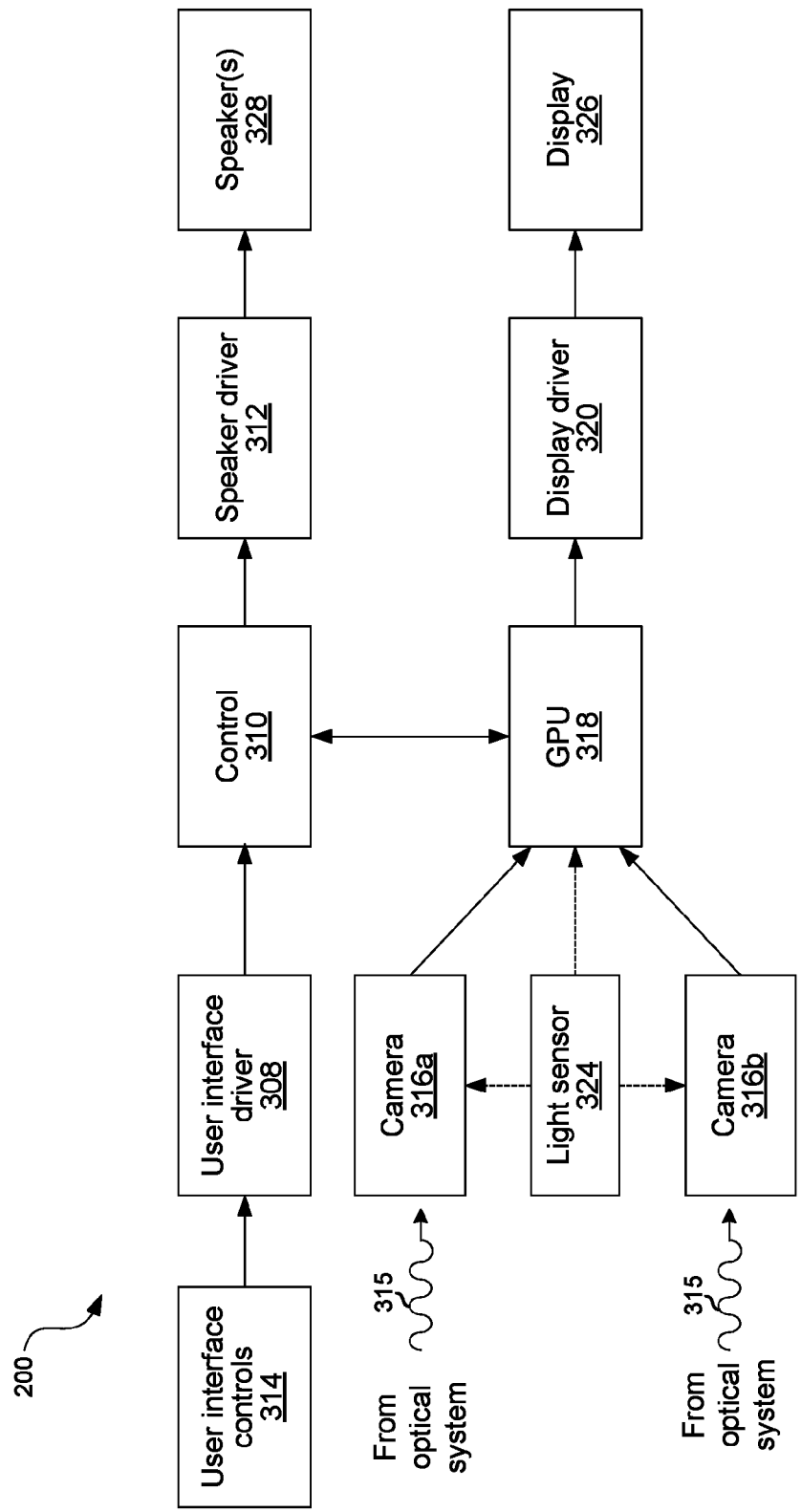
FIG. 3B shows example circuitry of the welding headwear of FIG. 2.
Figure 3C:
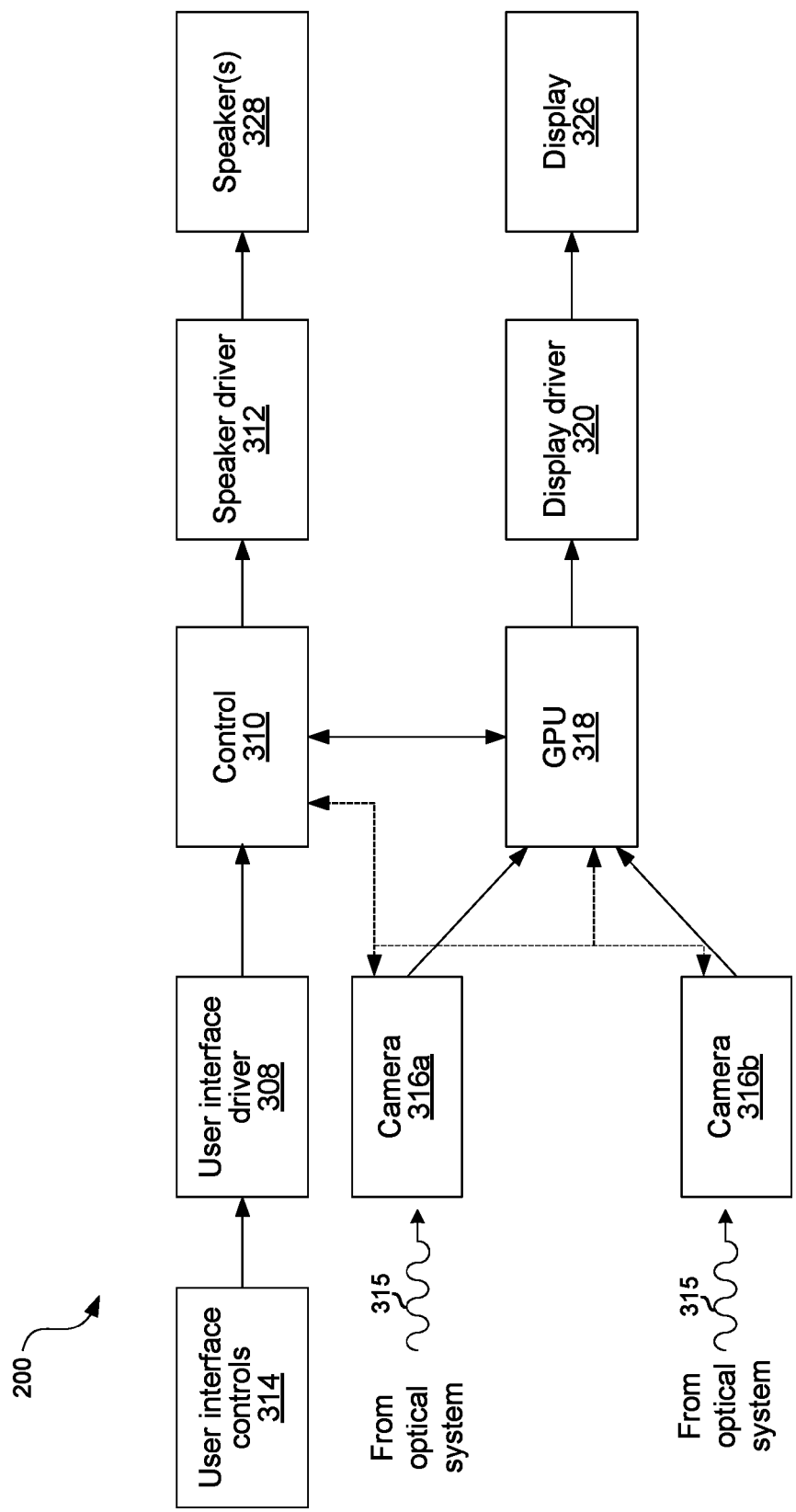
FIG. 3C shows example circuitry of the welding headwear of FIG. 2.

FIG. 2 shows example welding headwear in accordance with aspects of this disclosure. The example headwear 20 is a helmet comprising a shell 206 in or to which is mounted circuitry 200, example details of which are shown in FIGS. 3A-3C. In other implementations, some or all of the circuitry 200 might not be in the headwear 20, but can be in, for example, a welding torch (e.g., torch 27), welding power supply (e.g., equipment 12), welding apron, welding gloves, and/or any other welding related accessory.

In FIGS. 3A-3C, the circuitry 200 includes user interface controls 314, user interface driver circuitry 308, a control circuit 310, speaker driver circuitry 312, one or more speakers 328, one or more cameras 316a and 316b, a graphics processing unit (GPU) 318, display driver circuitry 320, and a display 326. In other embodiments, rather than a helmet, the headwear can be, for example, a mask, glasses, goggles, an attachment for a mask, an attachment for glasses, an attachment for goggles, or the like.

The user interface controls 314 can include, for example, one or more touchscreen elements, microphones, physical buttons, and/or the like that are operable to generate signals (e.g., electrical signals) in response to user input. For example, user interface controls 314 can include capacitive, inductive, or resistive touchscreen sensors mounted on the back of the display 326 (e.g., on the outside of the helmet 20) that enable a wearer of the helmet 20 to interact with user graphics displayed on the front of the display 326 (e.g., on the inside of the helmet 20).

The user interface driver circuitry 308 is operable to condition (e.g., amplify, digitize, etc.) signals from the user interface component(s) 314 for conveyance to the control circuit 310.

The control circuit 310 is operable to process signals from the user interface driver 308, the GPU 318, the light sensor 324 (FIG. 3A), and/or one or both of the cameras 316a and 316b (FIG. 3C). Signals from the user interface driver 308 can, for example, provide commands for setting various user preferences such as display settings (e.g., brightness, contrast, saturation, sharpness, gamma, etc.) and audio output settings (e.g., language, volume, stereo, mono, etc.). Signals from the GPU 318 can include, for example, information extracted from pixel data processed by the CPU, current settings/state/etc. of the GPU 318, and/or the like. Signals from the cameras 316a and 316b (FIG. 3C) can include, for example, information extracted from pixel data captured by the cameras, current settings/state/etc. of the cameras 316, and/or the like.

The control circuit 310 is also operable to generate data and/or control signals for output to the speaker driver 312, the GPU 318, and the cameras 316a and 316b (FIGS. 3A and 3C). Signals to the speaker driver 312 can include, for example, audio data for output via the speakers 328, control signals to adjust settings (e.g., volume) of the output audio, and/or the like. Signals to the GPU 318 can include, for example, control signals to select and/or configure pixel data processing algorithms to perform on the pixel data from the cameras 316a and 316b. Signals to the cameras 316 can include, for example, control signals to select and/or configure shutter speed, f-number, white balance, filter intensity, lens/shade darkness, and/or other settings of the cameras 316.

The speaker driver circuitry 312 is operable to condition (e.g., convert to analog, amplify, etc.) signals from the control circuitry 310 for output to one or more speakers 328 of the user interface components 314.

The cameras 316a and 316b are operable to capture electromagnetic waves of, for example, infrared, optical, ultraviolet, and/or radio frequency wavelengths. Each of cameras 316a and 316b can include, for example, an optical subsystem and two sets of one or more image sensors (e.g., two sets of one image sensor for monochrome or two sets of three image sensors for RGB). The optical subsystem can include, for example, a splitter that splits the incoming electromagnetic waves into two sets of electromagnetic waves of the same image that are sent to the image sensors. The splitting of the incoming electromagnetic waves allows for the processing of two images of the same image, but filtered with different dynamic ranges. One dynamic range can be configured for very bright portions of the image, such as the welding arc. Another dynamic range can be configured for the background of the image. The two images, each generated from a more limited dynamic range, can be combined to provide a high dynamic range (HDR) image. Multiple HDR images can be used to provide real-time or near real-time HDR video on the display of the helmet 20 (e.g., in an augmented reality application where the pixel data is overlaid on the real view instead of a mediated reality in which everything the viewer sees is a processed image).

Figure 4A:
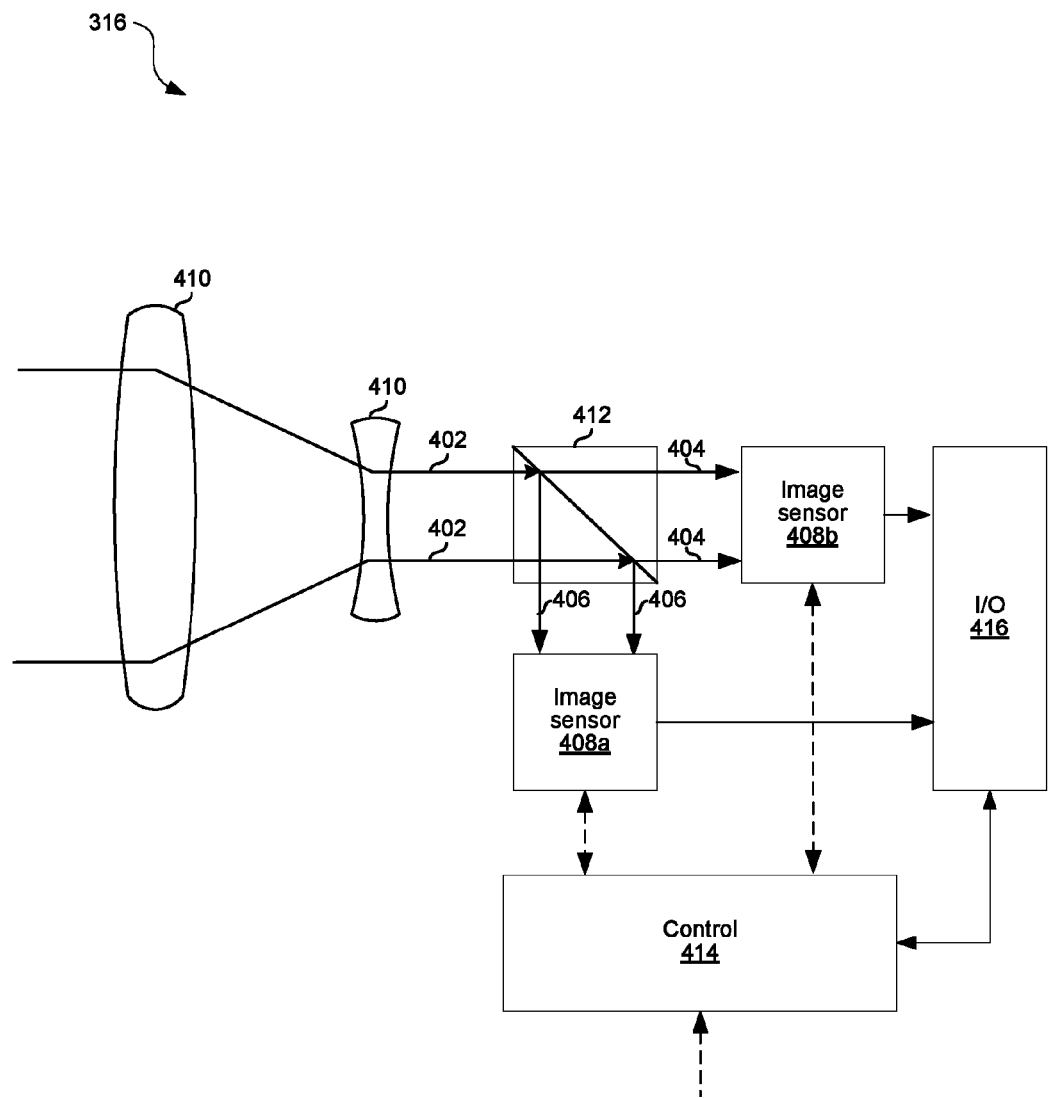
FIG. 4A shows example components of the welding headwear of FIG. 2.

Referring to FIG. 4A, an example implementation of a camera 316 is shown. The example implementation of the camera 316 shown in FIG. 4A includes lenses 410, beam splitter 412, image sensors 408a and 408b, control circuitry 414, and input/output circuitry 416. The image sensors 408a and 408b include, for example, CMOS or CCD image sensors operable to convert optical signals (or other types of electromagnetic signals) to digital pixel data and output the pixel data to input/output circuit 416. The input/output circuit 416 can output the pixel data in serial or parallel in accordance with protocols agreed on between the camera 316 and the GPU 318. The control circuitry 414 is operable to generate signals for configuring/controlling operation of the image sensors 408a and 408b and I/O circuit 416. The control circuit 414 can be operable to generate such control signals based on other control signals received from, for example, light sensor 324 and/or control circuit 310.

In operation, light beams 402 are focused onto beam splitter 412 by lenses 410. A first portion of beams 402 are reflected by the splitter 412 to arrive at image sensor 408a as beams 406. A second portion of beams 402 pass through the splitter 412 to arrive at image sensor 408b as beams 404. The image sensors 408a and 408b concurrently capture (e.g., their respective shutters are open for overlapping time periods) respective frames of the same image, but with different settings (e.g., different shutter speeds, different filter settings, etc.). The pixel data streams are then output to I/O circuit 416 which, in turn, relays them to GPU 318. The GPU 318 can then combine the two pixel streams to, for example, achieve an image with a higher dynamic range in some embodiments than can be achieved by either of the image sensors 408a and 408 individually.

In some embodiments, the GPU 318 can combine, using various algorithms to create an HDR image, the two pixel streams to achieve an HDR image from image sensors 408a and 408b, which individually might have more limited dynamic ranges.

In some embodiments, one of the image sensors 408b can be configured to see the details of the very bright portions (e.g., the arc, the weld puddle, etc.) of the combined image or provide a first dynamic range that covers the very bright arc or the puddle portion of the combined image; and the other image sensor 408a can be configured to see the details of the background (e.g., ambient areas, the workpiece, the cooling weld structures, etc.) or provide a second dynamic range that covers these less bright portions of the combined image. The combined image provides an HDR image including details in the both the very bright and less bright areas. The HDR image can also overcome imaging problems such as the bright areas bleaching out the dark areas, or the darkening of the bright areas at the expense of the details in the less bright areas of the image.

Figure 4B:
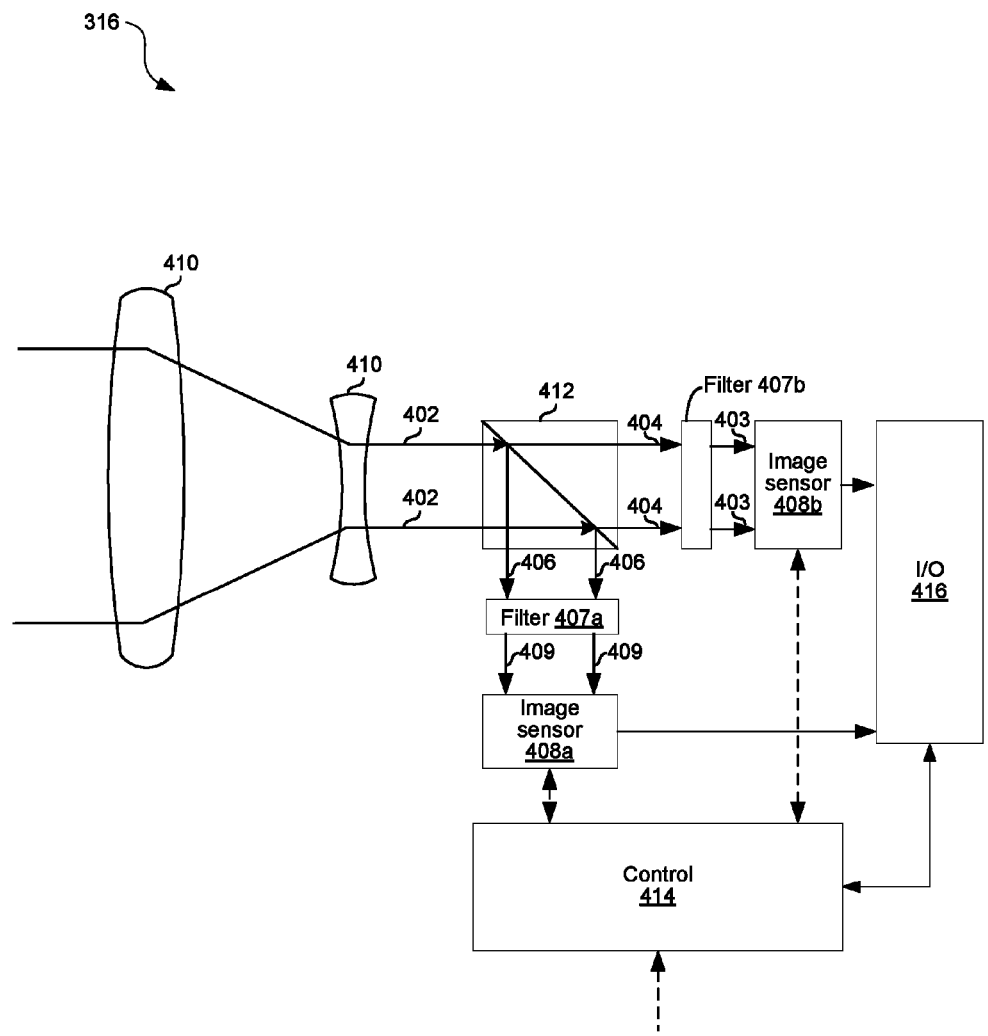
FIG. 4B shows example components of the welding headwear of FIG. 2.

FIG. 4B shows another embodiment of the camera 316. Similar to FIG. 4A, FIG. 4B also includes filters 407a and 407b that are disposed between the image sensor 408a and 408b and the splitter 412. In some embodiments, the filter 407a or 407b and the corresponding image sensor 408a or 408b can be integrated as part of a respective single device. One of the filters 407a can include a low density filter and can be used for the background, for example. The other filter 408a can include a high density filter and can be used for the arc and puddle piece of the image, for example. The image sensors 408a and 408b concurrently capture respective frames of the same image, but through different filters 407a and 407b with different characteristics (e.g., different dynamic ranges, different densities, different shade numbers, different exposures, etc.). The pixel data streams are then output to the I/O circuit 416 which, in turn, relays them to GPU 318. The GPU 318 can then combine the two pixel streams to, for example, achieve an HDR image that can exceed the dynamic ranges achieved by the individual components (e.g., the filter 407a and the image sensor 408a, and the filter 407b and the image sensor 408b).

Some embodiments provide that one or both of the filters 407a and 407b have fixed or preset densities. For example, one or both of the filters 407a and 407b can be preset to a particular filter density (e.g., each can be preset to a different filter density). In one example, one filter 407a can include a lens of shade #3 for picking out or extracting (e.g., providing definition for) the background, and one filter 407b can include a lens of shade #12 for picking out or extracting (e.g., providing definition for) the welding arc or the metal transfer. In some embodiments, one filter 407a provides greater definition to the background than to the welding arc or the metal transfer; one filter 407b provides greater definition to the welding arc or the metal transfer than to the background. Other embodiments provide that one or both of the filters 407a and 407b have variable filter densities (e.g., variable shade liquid crystal displays (LCDs)). Thus, for example, when the welding application is changed from a low power tungsten inert gas (TIG) welding arc to a high power open metal inert gas (MIG) welding arc, the variable filter densities can be changed to provide appropriate dynamic range. For example, for a low power welding application, the filter 407b associated with picking out the welding arc can be set to, for example, a lens shade #9; while for a high power welding application, the filter 407b associated with picking out the welding arc can be set to, for example, a darker lens shade #12.

Some embodiments also contemplate employing variable filters 407a and/or 407b with variable exposure times for the image sensors 408a and/or 408b. The variable filter densities and/or the variable exposure times can be adjusted based on, for example, settings on the equipment 12 (e.g., voltage, amperage, material thickness, material type, welding type, cutter type, wire feed speed, deposition rate, etc.) or by user interface controls 314 on the welding headwear 20. The filter densities and/or the variable exposure times can also be adjusted based on signals (e.g., related to arc brightness, background brightness, contrast, etc.) received from the image sensors 408a and 408b, the light sensor 324, the cameras 316a and 316b, the control 310, and/or the GPU 318. A real-time analysis of the brightness of the signals or the resulting images (e.g., an image received from a sensor, a combined image output by the GPU 318, etc.) can be a basis for dynamically changing the darkness of one or both of the filters 407a and 407b, and/or the exposure time of one or both image sensors 408a and 408b.

In some embodiments, components with more limited dynamic ranges than an HDR can be employed in the welding helmet or in some other display that is separate from the helmet to provide HDR quality images by combining signals from the non-HDR components. Such embodiments that combine outputs from non-HDR sensors (e.g., sensors with more limited dynamic ranges) can be more cost effective than employing an HDR sensor, for example. Some embodiments contemplate combining images from cost effective, high volume, linear sensors (e.g., sensors that are not individually HDR sensors) to provide HDR images and/or video.

In another example implementation, a plurality of splitters 412 are employed with a set of image sensors 408 for color for each camera 316. In yet another example implementation, more than two different and/or overlapping dynamic ranges can be employed. For example, through the use of a plurality of splitters 412, three different filters 407b with three different dynamic ranges can be used for different portions of the image. The combination of the three different images can provide an HDR image or video in which details are clearly visible not only for the brightest portions of the image (e.g., the arc) and the darkest portions of the image (e.g., background), but also some intermediary brightness (e.g., near the weld puddle).

In some example implementations, where stereo vision might not be needed, only a single camera 316 can be used.

Returning to FIGS. 3A-3C, the light sensor 324 (FIGS. 3A and 3B) includes circuitry operable to measure the intensity of light incident on the headwear 20. The light sensor 324 can include, for example, a photodiode or passive infrared (IR) sensor, along with associated drive electronics (e.g., amplifiers, buffers, logic circuits, etc.). The measured intensity (e.g., measured in candelas) can be used to determine when a welding arc is struck. In an example implementation, there can be multiple light sensors 324 which sense light intensity from multiple directions. For example, a first sensor 324 can sense the intensity of light incident on the front of the headwear 20 (light which can be directly incident on the headwear 20 from a welding arc) and a second sensor can sense the intensity of light incident on the back of the headwear 20 (which can be shielded from direct light from the welding arc). The different readings from various light sensors 324 can be used to determine information about the lighting environment, which can, in turn, be used for controlling the pixel data processing algorithms used for processing pixel data from the cameras 316a and 316b for presentation on the display 326.

The GPU 318 is operable to receive and process input pixel data from the cameras 316a and 316b. The processing of pixel data by the GPU 318 can extract information from the pixel data and convey that information to control circuit 310. The processing of pixel data by the GPU 318 can result in the generation of output pixel data for conveyance to the display driver 320. In an example implementation, the pixel data output from the GPU 318 to the display driver 320 (and ultimately to display 326) can provide a mediated-reality view for the wearer of the headwear 20. In such a view, the wearer experiences the video presented on the display 326 as if the wearer is looking through a lens, but with the image enhanced and/or supplemented by an on-screen display. The enhancements (e.g., adjust contrast, brightness, saturation, sharpness, gamma, etc.) can enable the wearer of the helmet 20 to see things s/he could not see with simply a lens (e.g., through contrast control). The on-screen display can include text, graphics, etc. overlaid on the video to, for example, provide visualizations of equipment settings received from the control circuit 310 and/or visualizations of information determined from the analysis of the pixel data. In another example implementation, the pixel data output from the GPU 318 can be overlaid on a real view seen through a transparent or semi-transparent lens (such as an auto-darkening lens found on conventional welding headwear). Such overlaid information can include text, graphics, etc. overlaid on the video to, for example, provide visualizations of equipment settings received from the control circuit 310 and/or visualizations of information determined from the analysis of the pixel data.

In an example implementation, the processing of pixel data by the GPU 318 can include the implementation of pixel data processing algorithms that, for example, determine the manner in which multiple input streams of pixel data from multiple cameras 316 are combined to form a single output stream of pixel data. Configuration of pixel data processing algorithms performed by GPU 318 can include, for example, configuration of parameters that determine characteristics (e.g., brightness, color, contrast, sharpness, gamma, etc.) of the streams prior to combining; characteristics (e.g., brightness, color, contrast, sharpness, gamma, etc.) of the combined stream; and/or weights to be applied to pixel data from each of the multiple streams during weighted combining of the multiple streams. In an example implementation using weighted combining of input pixel streams, the weights can be applied, for example, on a pixel-by-pixel basis, set-of-pixels-by-set-of-pixels basis, frame-by-frame basis, set-of-frames-by-set-of-frames basis, or some combination thereof. As one example, consider weighted combining of three frames of two input pixel streams where weights of 0, 1 are used for the first frame, weights 0.5, 0.5 are used for the second frame, and weights 1, 0 are used for the third frame. In this example, the first frame of the combined stream is the first frame of the second input stream, the second frame of the combined stream is the average of the second frames of the two input streams, and the third frame of the combined stream is the third frame of the first input stream. As another example, consider weighted combining of three pixels of two input pixel streams where weights of 0, 1 are used for the first pixel, weights 0.5, 0.5 are used for the second pixel, and weights 1, 0 are used for the third pixel. In this example, the first pixel of the combined stream is the first pixel of the second input stream, the second pixel of the combined stream is the average of the second pixels of the two input streams, and the third pixel of the combined stream is the third pixel of the first input stream.

In other example implementations, an augmented reality application can be provided in which pixel data comprising only predetermined objects (e.g., graphics, text, images captured by means other than the headwear 20, etc.) is rendered for output onto the display 306. Which objects are rendered, and/or characteristics (e.g., color, location, etc.) of those objects, can change based on whether the light sensor indicates the arc is present or not.

The display driver circuitry 320 is operable to generate control signals (e.g., bias and timing signals) for the display 326 and to process (e.g., level control synchronize, packetize, format, etc.) pixel data from the GPU 318 for conveyance to the display 326.

The display 326 can include, for example, two (e.g., in implementations using stereoscopic viewing) LCD, LED, OLED, E-ink, and/or any other suitable type of panels operable to convert electrical pixel data signals into optical signals viewable by a wearer of the helmet 20.

In operation, a determination of the intensity of light incident on the cameras 316a and 316b during capture of a pair of frames can be used for configuring the pixel data processing algorithm that performs combining of the two frames and/or can be used for configuring settings of the camera 316a and 316b for capture of the next pair of frames.

In the example implementations of FIGS. 3A and 3B, the light intensity is measured by one or more light sensors 324. Each light sensor can include, for example a photodiode or passive IR sensor that is sensitive to wavelengths in the visible spectrum. The measurement from the light sensor(s) 324 can then be used to configure pixel data capture settings (e.g., shutter speeds, f-numbers, white balance, etc.) of the cameras 316a and 316b. Additionally, or alternatively, the measurement from the light sensor(s) 324 can be used to select and/or configure pixel data processing algorithms performed on the captured pixel data by the GPU 318. In the example implementation of FIG. 3A, the measurement can be conveyed to the control circuit 310 which can then perform the configuration of the cameras 316a and 316b and/or the GPU 318. In the example implementation of FIG. 3B, the measurement from the light sensor(s) 324 can be conveyed directly to the cameras 316a and 316b and/or GPU 318, which can then use the measurement to configure themselves.

In the example implementation of FIG. 3C, rather than using a light sensor 324 that is distinct from the image sensors 408a and 408b, a measurement of light intensity is generated based on the pixel data captured by the cameras 316a and 316b. For example, each camera can calculate average luminance over groups of pixels of a frame and/or groups of frames. The calculated luminance value(s) can then be conveyed to the control circuit 310 and/or GPU 318 which can then configure the settings of the cameras 316a and 316b and/or configure the pixel data processing algorithms used to combine the pixel data from the two image sensors. The cameras 316a and 316b can also use the calculated luminance value(s) in a feedback loop for configuring their settings (such as timing and/or speed of an electronic and/or mechanical shutter, and/or some other electric, mechanical, or electromechanical operation or system in the cameras 316a and 316b).

The present method and/or system can be realized in hardware, software, or a combination of hardware and software. The present methods and/or systems can be realized in a centralized fashion in at least one computing system, or in a distributed fashion where different elements are spread across several interconnected computing systems. Any kind of computing system or other apparatus adapted for carrying out the methods described herein is suited. A typical combination of hardware and software can be a general-purpose computing system with a program or other code that, when being loaded and executed, controls the computing system such that it carries out the methods described herein. Another typical implementation can include an application specific integrated circuit or chip. Some implementations can include a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes can be made and equivalents can be substituted without departing from the scope of the present method and/or system. In addition, many modifications can be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

What is claimed is:

1. A dynamic range enhancement system for use in a welding application, comprising:
   a first filter disposed in a first path, wherein the first filter is configured to provide definition to a welding arc or a metal transfer;
   a second filter disposed in a second path, wherein the second filter has a lower density than the first filter;
   a first image sensor disposed in the first path and configured to receive filtered electromagnetic waves from the first filter;
   a second image sensor disposed in the second path and configured to receive filtered electromagnetic waves from the second filter; and
   a graphical circuit configured to combine signals from the first image sensor and the second image sensor.

2. The system according to claim 1, comprising a splitter configured to split incoming electromagnetic waves between the first path and the second path.

3. The system according to claim 1, wherein the graphical circuit is configured to combine the signals from the first image sensor and the second image sensor to provide a dynamic range image or video that has a dynamic range that is greater than the dynamic range of the first image sensor alone or the second image sensor alone.

4. The system according to claim 3, wherein the dynamic range image or video is displayed on a welding helmet display.

5. The system according to claim 3, wherein the dynamic range image or video is displayed as part of a mediated-reality display for a wearer of a welding helmet.

6. The system according to claim 3, wherein the dynamic range image or video is displayed as part of an augmented-reality display for a wearer of a welding helmet.

7. The system according to claim 1, wherein the first filter is configured to provide greater definition to a welding arc or a metal transfer than a background.

8. The system according to claim 1, wherein the second filter is configured to provide definition to a background.

9. The system according to claim 1, wherein the second filter is configured to provide greater definition to a background than a welding arc or a metal transfer.

10. The system according to claim 1, wherein the first filter or the second filter is preset to a particular fixed lens shading.

11. The system according to claim 1, wherein the first filter or the second filter is configured to provide variable lens shading.

12. The system according to claim 1, wherein the first filter or the second filter is configured to provide variable lens shading based on one or more welding settings on welding equipment.

13. The system according to claim 1, wherein the one or more welding settings on the welding equipment include one or more of the following: a voltage setting, an amperage setting, a material thickness setting, a material type setting, a welding type setting, a wire feed speed, and a deposition rate setting.

14. The system according to claim 1, wherein the first filter or the second filter is configured to provide variable lens shading based on a measurement of an arc brightness.

15. The system according to claim 1, wherein the first filter or the second filter is configured to provide variable lens shading based on a measurement of a background brightness.

16. A method for displaying in a welding application, comprising:
    providing a first filter in the first path and a second filter in the second path, wherein the second filter has a lower density than the first filter, wherein the first filter is configured to provide definition to a welding arc or a metal transfer;
    receiving, by a first image sensor, filtered electromagnetic waves from the first filter;
    receiving, by a second image sensor, filtered electromagnetic waves from the second filter; and
    combining, by a graphical circuit, signals from the first image sensor and the second image sensor.

17. The method according to claim 16, comprising splitting, by a splitter, incoming electromagnetic waves between the first path and the second path.

18. The method according to claim 16, wherein the combining comprises combining, by the graphical circuit, signals from the first image sensor and the second image sensor to provide a dynamic range image or video that has a dynamic range that is greater than the dynamic range of the first image sensor alone or the second image sensor alone.

19. The method according to claim 18, comprising:
    displaying the dynamic range image or video on a welding helmet display.

20. The method according to claim 18, comprising:
    displaying the dynamic range image or video on a mediated-reality display or an augmented-reality display for a wearer of a welding helmet.

21. The method according to claim 16, comprising:
    providing definition to a welding arc or a metal transfer in the first path; and
    providing definition to a background in the second path.

22. The method according to claim 16, comprising:
    varying lens shading of the first filter based on one or more welding settings including one or more of the following: a voltage setting, an amperage setting, a material thickness setting, a material type setting, a welding type setting, a wire feed speed, and a deposition rate setting.

23. The method according to claim 16, comprising:
    measuring a brightness of an arc; and
    varying lens shading of the first filter based on the measured brightness of the arc.

24. A welding helmet display system, comprising:
    a first filter disposed in a first path, wherein the first filter is configured to provide definition to a welding arc or a metal transfer;
    a second filter disposed in a second path, wherein the second filter has a lower density than the first filter;
    a first image sensor disposed in the first path and configured to receive filtered electromagnetic waves from the first filter;
    a second image sensor disposed in the second path and configured to receive filtered electromagnetic waves from the second filter; and
    a circuit configured to combine signals based on the incoming electromagnetic waves from the first path and the second path.

25. The system according to claim 24, comprising a splitter configured to split incoming electromagnetic waves between the first path and the second path.

26. The system according to claim 24, wherein the circuit is configured to combine the signals from the first path and the second path to provide a dynamic range image or video that has a dynamic range that is greater than the dynamic range of the first path alone or the path alone.

27. The system according to claim 26, comprising a welding helmet display on which the dynamic range image or video is displayed.

28. The system according to claim 24, wherein the first filter or the second filter is configured to provide variable lens shading based on one or more welding equipment settings including one or more of the following: a voltage setting, an amperage setting, a material thickness setting, a material type setting, a welding type setting, a wire feed speed, and a deposition rate setting.

29. The system according to claim 24, wherein the first filter or the second filter is configured to provide variable lens shading based on a measurement of an arc brightness or a measurement of a background brightness.

\* \* \* \* \*